(12) United States Patent
     Marshall (10) Patent No.: US 12,257,200 B2
(45) Date of Patent: Mar. 25, 2025

(54) BED PAN ASSEMBLY WITH EXCRETION ANALYZATION

(71) Applicant: NEOWE RESEARCH AND DEVELOPMENT, INC., Dania Beach, FL (US)

(72) Inventor: Michelle Marshall, Dania Beach, FL (US)

(73) Assignee: Neowe Research and Development, Inc., Hollywood, FL (US)

( * ) Notice: Subject to any disclaimer, the term of this patent is extended or adjusted under 35 U.S.C. 154(b) by 0 days.

(21) Appl. No.: 18/024,453

(22) PCT Filed: Aug. 4, 2021

(86) PCT No.: PCT/US2021/044579
§ 371 (c)(1),
(2) Date: Mar. 2, 2023

(87) PCT Pub. No.: WO2022/031873
PCT Pub. Date: Feb. 10, 2022

(65) Prior Publication Data
US 2023/0310243 A1     Oct. 5, 2023

Related U.S. Application Data

(60) Provisional application No. 63/060,915, filed on Aug. 4, 2020.

(51) Int. Cl.
    *A61B 5/00*           (2006.01)
    *A61B 5/20*           (2006.01)
    (Continued)

(52) U.S. Cl.
CPC ............ *A61G 9/003* (2013.01); *A61B 5/0002* (2013.01); *A61B 5/0075* (2013.01); *A61B 5/208* (2013.01);
(Continued)

(58) Field of Classification Search
CPC .... A61G 9/003; A61B 5/0002; A61B 5/0075; A61B 5/208; A61B 5/392; A61B 10/0038;
(Continued)

(56) References Cited

U.S. PATENT DOCUMENTS 6,372,951 B1 *   4/2002   Ter-Ovanesyan ....... A61L 15/26
                                                        600/595
6,407,308 B1 *   6/2002   Roe ......................... A61L 15/20
                                                         604/362

(Continued)

FOREIGN PATENT DOCUMENTS

JP          2014206002 A     10/2014
WO       2014047581 A1     9/2013

*Primary Examiner* — May A Abouelela
(74) *Attorney, Agent, or Firm* — Mark C. Johnson; Johnson | Dalal (57) ABSTRACT

A bed pan assembly with excretion analyzation beneficially configured to collect, read, sample, analyze, and/or notify one or more desired users of one or more targeted properties of a stool or urine sample and comprising a portable bed pan housing with a bottom wall, a sidewall, an excretion storage cavity, and at least one analyzing sensor operably configured to detect at least one of a targeted stool or urine property from a stool or urine specimen received within the excretion storage cavity, communicatively couplable to a remote electronic communication device over a wireless network, and operably configured to communicate an electronic notification of the at least one of the targeted stool or urine property to the remote electronic communication device over the wireless network. The analyzing sensors may be specifically, operably configured to detect excreta occult blood, urine flowrate, oxyhemoglobin, deoxyhemoglobin, melanin, weight, or movement as the targeted properties.

11 Claims, 9 Drawing Sheets

(51) Int. Cl.
  *A61B 5/392* (2021.01)
  *A61B 10/00* (2006.01)
  *A61G 9/00* (2006.01)

(52) U.S. Cl.
  CPC .......... *A61B 5/392* (2021.01); *A61B 10/0038* (2013.01); *A61B 2562/0204* (2013.01)

(58) Field of Classification Search
  CPC .......... A61B 2562/0204; A61B 10/007; G01N 33/4833; G01N 33/493
  See application file for complete search history.

(56) References Cited

U.S. PATENT DOCUMENTS

| | | | |
|---|---|---|---|
| 7,891,030 B1* | 2/2011 | Sutton | A47K 11/06 4/483 |
| 8,303,554 B2* | 11/2012 | Tsai | A61B 5/445 604/347 |
| 10,022,286 B2* | 7/2018 | Marshall | A61G 9/003 |
| 10,130,293 B2 | 11/2018 | Hidas | |
| 10,145,787 B2 | 12/2018 | Wellysun | |
| 2011/0185489 A1* | 8/2011 | Partington | A61G 9/003 4/450 |
| 2013/0158365 A1* | 6/2013 | Chey | A61B 5/14503 600/595 |
| 2014/0082832 A1* | 3/2014 | Marshall | A61G 9/003 4/452 |
| 2020/0268302 A1* | 8/2020 | Oh | A61B 5/227 |
| 2022/0151510 A1* | 5/2022 | Kashyap | H04N 7/188 |

\* cited by examiner

BED PAN ASSEMBLY WITH EXCRETION ANALYZATION

FIELD OF THE INVENTION

The present invention relates generally to bedpan assemblies, and, more particularly, relates to bedpan assemblies operably configured to collect and analyze excretion samples.

BACKGROUND OF THE INVENTION

As those of skill in the art will appreciate, there are known devices available to examine a stool culture to look for bacteria, viruses, or other germs (collectively referred to as "targeted property") that could adversely affect a human user. Those of skill in the art will also appreciate that there are devices operably configured to test a user's urine for targeted properties such as levels of protein, glucose, and blood as well as to identify signs of infection. Again, these targeted properties can be indicative of adverse conditions or problems a user is experiencing, such as diabetes, preeclampsia (high blood pressure), viruses, kidney and bladder infection, and/or other medical or health issues. Generally, however, these devices are utilized in a separate process subsequent to the initial step of collecting a user's urine or stool sample. In other words, a user must first produce a urine or stool sample, at which point a medical professional uses a known device to test the sample for targeted properties. In the case of bedridden patients, a bedpan assembly may be utilized to collect the sample which is then tested using known devices. Bedpans are utilized by many users or patients, and conventionally include a receptacle used for the toileting of a bedridden patient in a health care facility. Bedpans are usually made of metal, glass, ceramic, or plastic and can be used for both urinary and fecal discharge. For example, many diseases can confine a patient to bed, necessitating the use of bedpans, including Alzheimer's disease, Parkinson's disease, stroke, and dementia. Additionally, many patients may be confined to a bed temporarily as a result of a temporary illness, injury, or surgery, thereby necessitating the use of a bedpan. Bedpans may be positioned under the bedridden patient or in close proximity for use. Existing bedpan assemblies, however, are characterized by a significant limitation insofar as they do not consolidate the functions of collecting, testing, reading, and analyzing the sample, as well as notifying one or more desired users of one or more of the targeted properties, into one composite assembly. See, e.g., Yan (Wellysun Inc.), U.S. Pat. No. 10,145,787 B2 (Dec. 4, 2018); Sekine (Toto Ltd 70%, Toto Ltd), U.S. Pub. No. 2020/0008786 A1.

Therefore, a need exists to overcome the problems with the prior art as discussed above.

SUMMARY OF THE INVENTION

The invention provides a bed pan assembly with excretion analyzation that overcomes the hereinafore-mentioned disadvantages of the heretofore-known devices and methods of this general type and that is beneficially configured to collect, read, sample, analyze, and/or notify one or more desired users of one or more of the targeted properties of a stool or urine sample, more specifically the presence of said targeted properties or when a threshold amount of a targeted property is exceeded.

With the foregoing and other objects in view, there is provided, in accordance with the invention, a bed pan assembly with excretion analyzation comprising a portable bed pan housing with a bottom wall having a bottom inner surface; a sidewall having an inner sidewall surface surrounding the bottom inner surface to define an excretion storage cavity and having an upper surface surrounding the sidewall for supporting a weight of a user; and at least one analyzing sensor operably coupled to at least one of the bottom wall and the sidewall of the bed pan housing, operably configured to detect at least one of a targeted stool property from a stool specimen received within the excretion storage cavity and a targeted urine property from a urine specimen received within the excretion storage cavity, communicatively couplable to a remote electronic communication device over a wireless network, and operably configured to communicate an electronic notification of the at least one of the targeted stool property and the targeted urine property to the remote electronic communication device over the wireless network.

In accordance with a further feature, the at least one analyzing sensor is directly connected to the sidewall and further comprises a camera oriented at least partially toward the bottom inner surface, wherein the least one analyzing sensor is operably configured to detect excreta occult blood as the targeted stool property.

In accordance with another feature of an exemplary embodiment, the at least one analyzing sensor is directly connected to the sidewall and further comprises a light spectroscopy unit operably configured to detect excreta occult blood as the targeted stool property.

In accordance with another embodiment of the present invention, the at least one analyzing sensor is directly connected to the sidewall and further comprises a light spectroscopy unit oriented at least partially toward the upper surface and operably configured to detect reflected light energy from a user's skin and relative or absolute concentration of at least one of oxyhemoglobin (oxyHb), deoxyhemoglobin (deoxyHb), and melanin therein.

In accordance with a further feature of the present invention, the at least one analyzing sensor further comprises a microphone operably configured to detect vibration within the at least one of the bottom wall and the sidewall of the bed pan housing to measure flowrate of urine within the excretion storage cavity as the targeted urine property.

In accordance with another feature, the at least one analyzing sensor is directly coupled to the sidewall, disposed proximal to the upper surface, and operably configured to detect weight and movement of a user supported on the upper surface of the bed pan housing.

In accordance with one embodiment of the present invention, the at least one analyzing sensor is directly coupled to the sidewall, disposed proximal to the upper surface, and operably configured to measure changes in electrical activity of a user's external anal sphincter, thereby predicting impending elimination of body waste from the user, the least one analyzing sensor operably configured to communicate the electronic notification of the measured changes in electrical activity to the remote electronic communication device over the wireless network.

In accordance with another embodiment of the present invention, the upper surface of the sidewall is substantially planar and defines an upper plane parallel and non-coplanar with a bottom plane defined by a lower terminal surface of the bed pan housing, the lower terminal surface opposing the upper surface of the sidewall.

In accordance with another feature, an embodiment of the present invention includes a drain defined thereon and with a filter cover superimposing the drain; and a lower chamber defined thereon and spatially separated from the excretion storage cavity by the filter cover, wherein the at least one analyzing sensor is disposed within the lower chamber and operably configured to detect the targeted urine property.

In accordance with a further feature of one embodiment, the bed pan assembly also comprises an assembly cover selectively removably couplable to the portable bed pan housing, the assembly cover having an upper assembly cover surface, a lower assembly cover surface opposing the upper assembly cover surface, and an aperture proportionately sized and shaped with respect to the excretion storage cavity.

In accordance with yet another feature, an exemplary embodiment of the bed pan assembly includes a selectively removable retention member interposed between the assembly cover and the portable bed pan housing, the selectively removable retention member operably configured to retain a disposable waste bag thereon.

Although the invention is illustrated and described herein as embodied in a bed pan assembly with excretion analyzation, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the assembly. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the bed pan assembly from a proximal end to a distal end, wherein "transverse" should be understood to mean a direction corresponding to a direction opposite of the longitudinal direction, i.e., side-to-side. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION OF INVENTION

The invention described herein provides a smart bed pan assembly with excretion analyzation that overcomes known disadvantages of those known devices and methods of this general type and that efficiently and effectively samples, analyzes, and/or notifies one or more user(s) of a triggering sample event. The attached figures are incorporated in and form part of the specification and serve to further illustrate various embodiments and explain various principles and advantages all in accordance with the present invention.

Figure 1:
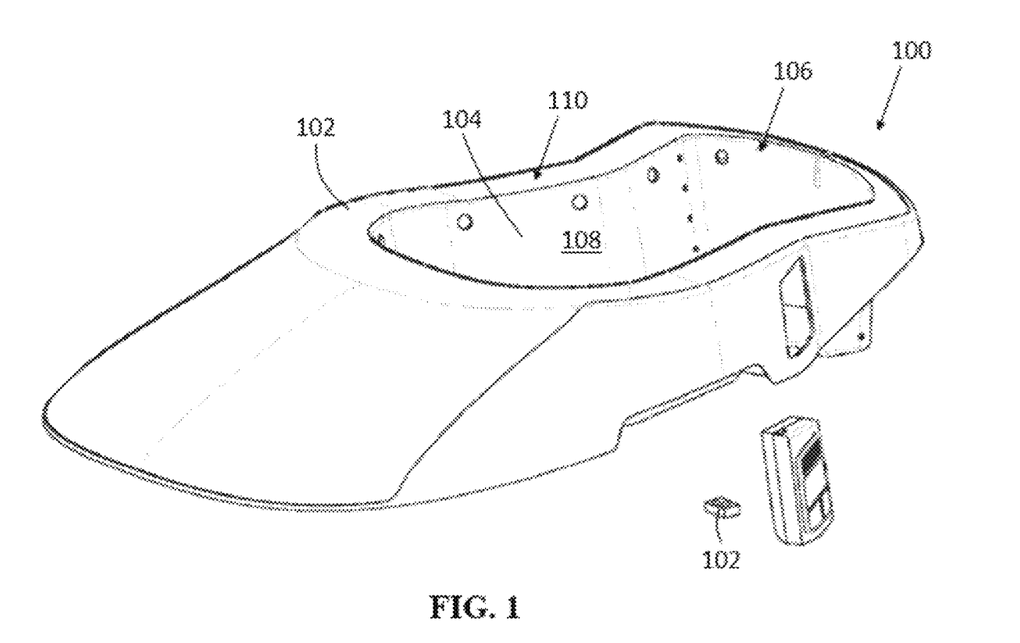
FIG. 1 is a perspective side view of an exemplary embodiment of a bed pan assembly with excretion analyzation, in accordance with the present invention.
Figure 2:
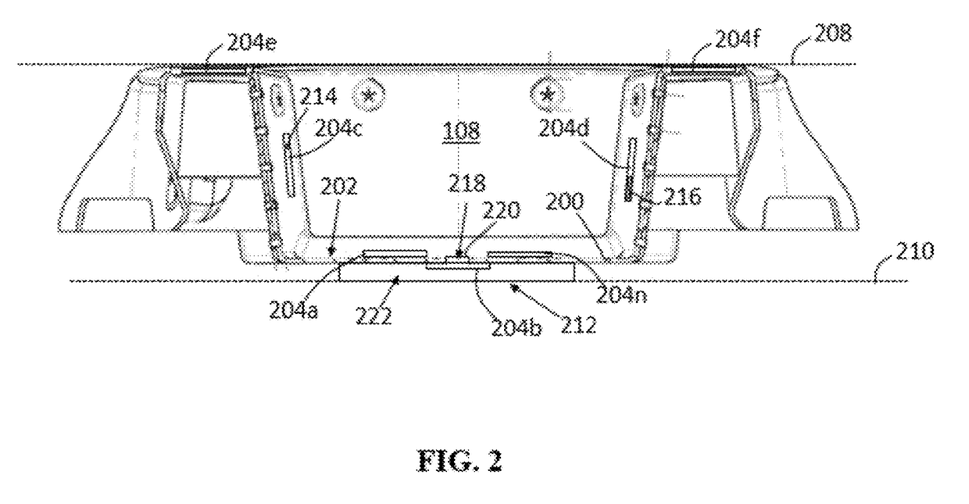
FIG. 2 is a cross-sectional front view of a bed pan assembly with excretion analyzation, in accordance with an exemplary embodiment of the present invention.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components. The first example of a smart bed pan assembly, as shown in FIG. 1, includes a bed pan assembly 100 with many components features as disclosed in U.S. Pat. No. 10,022,286 B2 (Marshall), which is incorporated herein by reference. With reference to FIGS. 1-2 and the block diagrams in FIGS. 3-4, to effectuate the same, the bed pan assembly 100 with excretion analyzation includes a portable bed pan housing 102 with a bottom wall 200 having a bottom inner surface 202 and a sidewall 104 having an inner sidewall surface 106 surrounding the bottom inner surface 202 to define an excretion storage cavity 108 and having an upper surface 110 surrounding the sidewall 104 for supporting a weight of a user. In one embodiment, the portable bed pan housing 102 is constructed and arranged of a flexible material, including but not limited to, plastics, polymers, combinations thereof, and the like. In one embodiment, the upper surface 110 of the sidewall 104 is substantially planar and defines an upper plane 208 parallel and non-coplanar with a bottom plane 210 defined by a lower terminal surface 212 of the bed pan housing 102, the lower terminal surface 212 opposing the upper surface 110 of the sidewall 104. The foregoing configuration substantially prevents spillage of the stool or urine sample disposed within the excretion storage cavity 108, improves handling, and allows a user to more easily and readily maneuver the bed pan assembly 100 during use so as to substantially prevent spillage of the stool or urine sample from the excretion storage cavity 108. The portable bed pan housing 102 has a length approximately between 16 inches and 19 inches, with an exemplary length of 17.6 inches, and a height approximately between 4 inches and 6 inches, with an exemplary height of 5.12 inches. In some embodiments, the portable bed pan housing 102 may also comprise handle members or handle grooves disposed on an outer sidewall surface of the sidewall 104.

As best seen in FIGS. 1-2, the portable bed pan housing 102 further comprises at least one analyzing sensor 204a-n, wherein "n" refers to any number greater than one, operably coupled to at least one of the bottom wall 200 and the sidewall 104 of the bed pan housing 102, operably configured to detect at least one of a targeted stool property from a stool specimen received within the excretion storage cavity 108 and a targeted urine property from a urine specimen received within the excretion storage cavity 108, communicatively couplable to a remote electronic communication device 404 over a wireless network 400, and operably configured to communicate an electronic notification of the at least one of the targeted stool property and the targeted urine property to the remote electronic communication device over the wireless network 400. The analyzing sensors 204a-n utilizes non-destructive means that may include spectroscopy and measurement of multi-component systems for material concentration or for modeled physical/chemical properties. The interacting with materials is essentially a spectrum of electromagnetic waves with different wavelengths. Fundamentals of bands absorbed by materials are found in Mid-InfraRed (MIR) region of light (wavelengths >3,500 nm). The Near InfraRed (NIR) region of light is absorbed by the energy bands related to the overtones and combinations of the fundamentals bands. There are many known fecal and urine analyzing sensors disclosed in the art, primarily utilized with toilets, but no known sensors have been disclosed that utilize a sample from a bed pan assembly that is operably configured to notify users, e.g., physicians, of the results of said samples. See, e.g., Ogura et al., U.S. Pat. No. 4,636,474, Nakayama et al., U.S. Pat. No. 5,730,140, Roe et al., U.S. Pat. No. 6,149,636, Roe et al., U.S. Pat. No. 6,342,037, Hasegawa et al., U.S. Pat. No. 10,571,470.

The analyzing sensors 204a-n are operably configured to sample and analyze urine and/or stool for the above-described one or more targeted properties, e.g., bacteria, viruses, germs, etc. In preferred embodiments, the analyzing sensors 204a-n may be disposed centrally on the bottom wall 200 or may be disposed on the sidewall 104 of the bed pan housing 102. Each analyzing sensor 204a-n may include a circuit board assembly 300 to effectuate the sampling, analyzing, and/or notification features of the present invention. Preferably, the circuit board assembly 300 is disposed in a watertight housing and/or environment, e.g., within a housing that includes one or more channels and/or apertures operably configured to draw in liquid and/or solid particulate. The circuit board assembly is electrically coupled to a power source 302, e.g., a two-coin power cell 250 mAH batteries. The circuit board assembly also includes a transmitter or network interface 306 for relaying data relating to the targeted property or properties from the analyzing sensors 204a-n and/or an indication that a threshold amount of the targeted property has been met or exceeded. The circuit board assembly 300 may be composed of one or more PCB(s) (or printed circuit boards).

Figure 3:
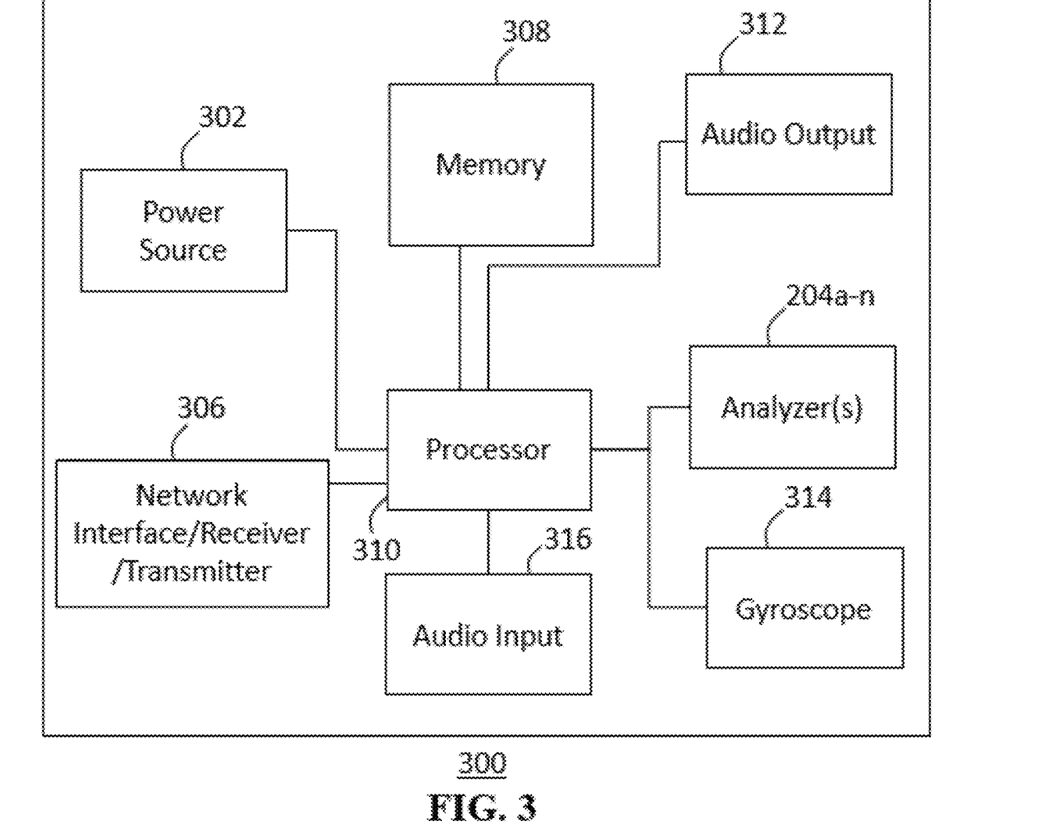
FIG. 3 is a block diagram of an exemplary bed pan assembly with excretion analyzation, in accordance with the present invention.

One exemplary circuit board assembly 300 (as seen in FIG. 3) may also include a memory 308, a processing device 310, and an audio or vibrational output 312. The network interface(s) 306 may include one or more network interface cards (NIC) or a network controller. In some embodiments, the network interface 306 may include a personal area network (PAN) interface. The PAN interface may provide the capability for the circuit board to communicate over a network 400 using a short-range communication protocol, for example, a Bluetooth communication protocol, which may also operate as a receiver, transmitter, and/or transceiver. The PAN interface may permit the circuit board assembly 300 to connect wirelessly to another electronic computing device, e.g., software application, via a peer-to-peer connection or other communicatively coupled configuration.

Figure 4:
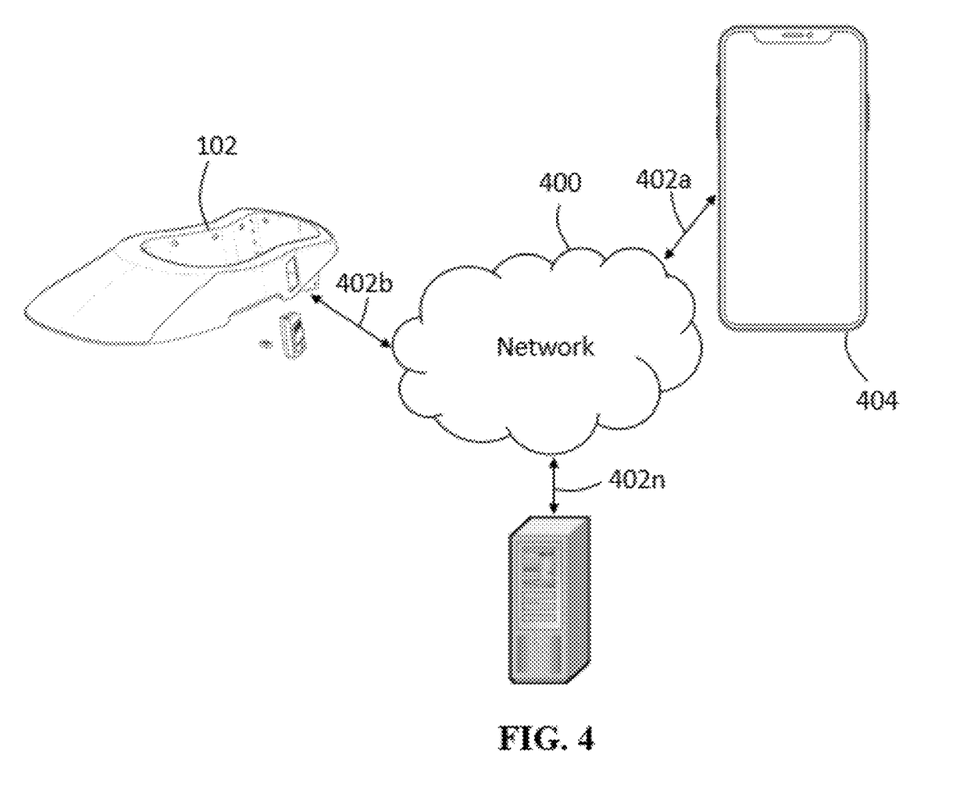
FIG. 4 is a block diagram of an exemplary distributed data processing network with a bed pan assembly, a mobile electronic device, and a server, in accordance with an embodiment of the present invention.
Figure 5:
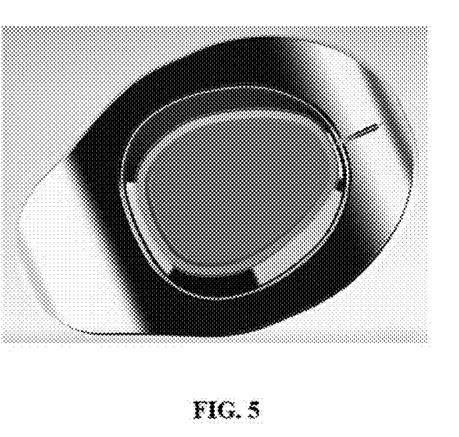
FIG. 5 is an elevational top view of an exemplary bed pan assembly with excretion analyzation, in accordance with the present invention.
Figure 6:
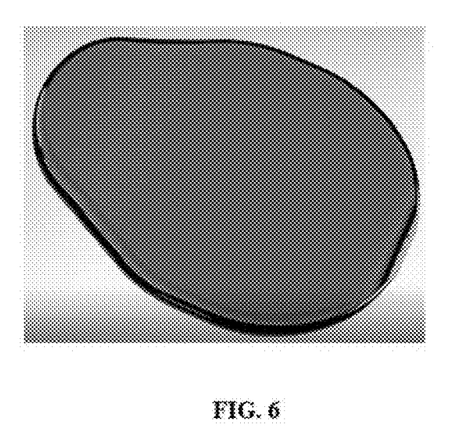
FIG. 6 is an elevational bottom view of an exemplary bed pan assembly with excretion analyzation, in accordance with the present invention.
Figure 7:
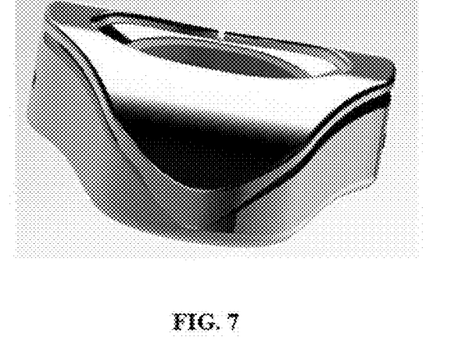
FIG. 7 is a perspective front view of an exemplary bed pan assembly with excretion analyzation, in accordance with the present invention.
Figure 8:
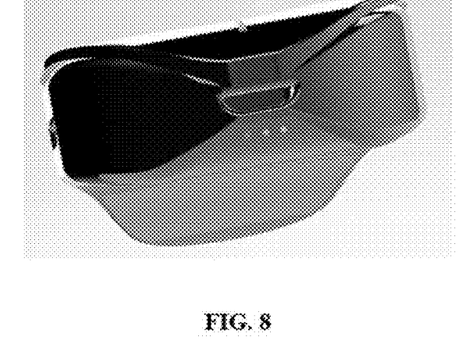
FIG. 8 is a perspective rear view of an exemplary bed pan assembly with excretion analyzation, in accordance with the present invention.
Figure 9:
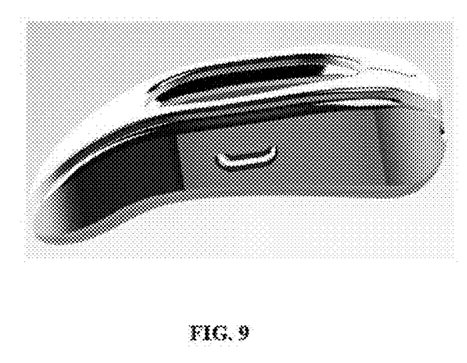
FIGS. 9-10 are elevational side views of an exemplary bed pan assembly with excretion analyzation, in accordance with the present invention.
Figure 10:
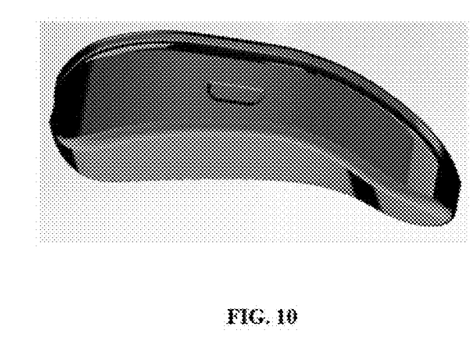
Figure 11:
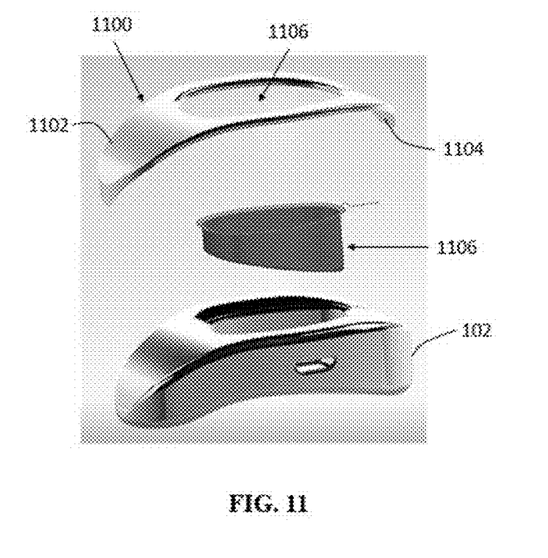
FIGS. 11-12 are exploded side views of two embodiments of a bed pan assembly with excretion analyzation, in accordance with the present invention.
Figure 12:
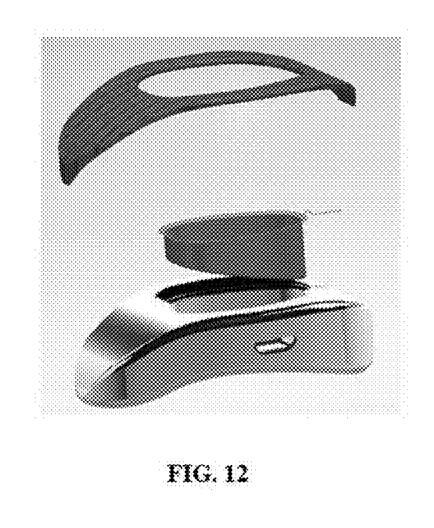
Figure 13:
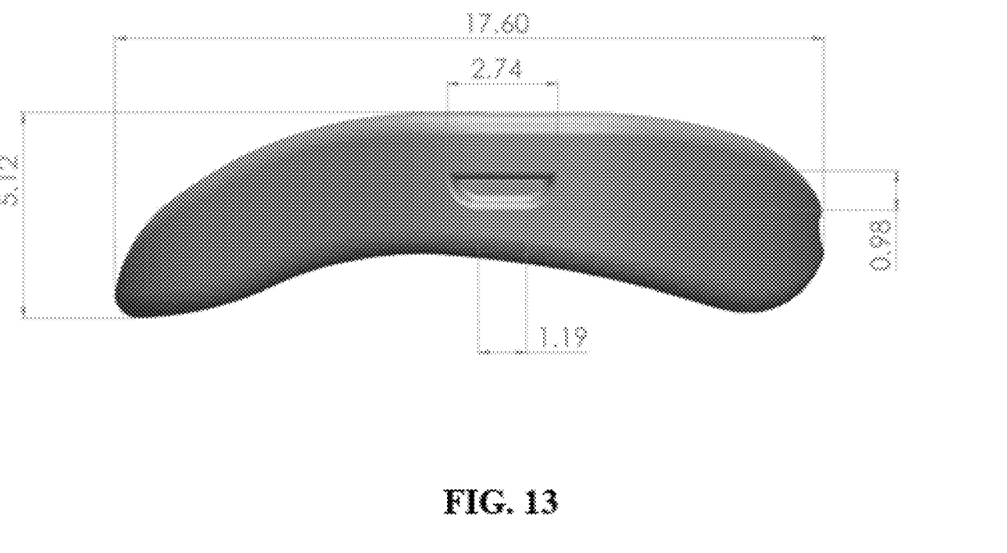
FIG. 13 is an elevational side view of an exemplary bed pan assembly with excretion analyzation, in accordance with the present invention.

The network interface(s) 306 may also include a local area network (LAN) interface. The LAN interface may be, for example, an interface to a wireless LAN, such as a Wi-Fi network. In one embodiment, there is a wireless LAN that provides the circuit board assembly 300 with access to the Internet for receiving and sending inputs/messages to, for example, an administrator server or other electronic device over, for example, the Internet. The range of the LAN interface may generally exceed the range available via the PAN interface. Typically, a connection between two electronic devices via the LAN interface may involve communication through a network router or other intermediary device. Exemplary connections between devices over the network 400 are depicted in FIG. 4 with arrows 402*a-n*. In one embodiment, the circuit board and an electrical computing device, e.g., mobile phone, may be paired, or establishing a communication linkage, before the user intends to use the bed pan assembly 100 and/or after a notification or alert, using the audio/visual output 312, is initiated. The pairing may be through an RFID means.

Additionally, the network interface(s) 306 may include the capability to connect to a wide area network (WAN) via a WAN interface. The WAN interface may permit a connection to a cellular mobile communications network. The WAN interface may include communications circuitry, such as an antenna coupled to a radio circuit having a transceiver for transmitting and receiving radio signals via the antenna. The radio circuit may be configured to operate in a mobile communications network, including but not limited to global systems for mobile communications (GSM), code division multiple access (CDMA), wideband CDMA (WCDMA), and the like.

The memory 308 associated with the circuit board assembly 300 may be, for example, one or more buffer, a flash memory, or non-volatile memory, such as random-access memory (RAM). The circuit board assembly 300 may also include non-volatile storage. The processing device 310 can be, for example, a central processing unit (CPU), a microcontroller, or a microprocessing device, including a "general purpose" microprocessing device or a special purpose microprocessing device. The processing device 310 is operably configured to execute code stored in the memory to carry out operation/instructions of the analyzer(s) or other electrical components operably coupled to the circuit board. The processing device 310 may provide the processing capability to execute the P2P network described above. The remote electronic communication device 404 may be a computer, mobile electronic device, or other comparable device, the remote electronic communication device 404 may be considered an example implementation of other devices and components within the circuit board assembly 300 depicted in FIG. 3.

In accordance with a further feature of the present invention, the at least one analyzing sensor 204*c* is directly connected to the sidewall 104 and includes a camera 214 oriented at least partially toward the bottom inner surface 202, wherein the at least one analyzing sensor 204*a-n* is operably configured to detect excreta occult blood as the targeted stool property. A fecal occult blood test (FOBT) is a lab test used to check stool samples for hidden (occult) blood. Occult blood in the stool may indicate colon cancer or polyps in the colon or rectum-though not all cancers or polyps bleed.

Blood in the stool means there is likely some kind of bleeding in the digestive tract. It may be caused by a variety of conditions, including polyps, hemorrhoids, diverticulosis, ulcers, and colitis. The two main types of fecal occult blood tests are the guaiac smear method (gFOBT) and the immunochemical method (iFOBT or FIT). The analyzing sensors 204*a-n* may be operably configured to detect excreta occult blood using gFOBT, iFOBT or FIT, or another comparable method known to those skilled in the art.

In one embodiment, the analyzing sensors 204*a-n* comprise a light spectroscopy unit 216 operably configured to detect excreta occult blood as the targeted stool property. Spectroscopy involves the splitting of light (or more precisely electromagnetic radiation) into its constituent wavelengths (a spectrum). Modern spectroscopy uses diffraction grating to disperse light, which is then projected onto CCDs (charge-coupled devices). The 2D spectra are easily extracted from this digital format and manipulated to produce 1D spectra that contain an impressive amount of useful data. The light spectroscopy unit 216 may detect interactions between particles such as electrons, protons, and ions, as well as their interaction with other particles as a function of their collision energy, to detect excreta occult blood. In another embodiment, the at least one analyzing sensor 204*d* is directly connected to the sidewall 104 and comprises the light spectroscopy unit 216 oriented at least partially toward the upper surface 110 and operably configured to detect reflected light energy from a user's skin and relative or absolute concentration of at least one of oxyhemoglobin (oxyHb), deoxyhemoglobin (deoxyHb), and melanin therein. Oxyhemoglobin is a bright red substance formed by the combination of hemoglobin with oxygen, present in oxygenated blood. The normal oxygen saturation of the blood is around 98 to 100 percent. The body needs enough oxygen to keep the blood adequately saturated, so that cells and tissues get enough oxygen to function properly. Cells and tissues can neither "save up" nor "catch up" on oxygen—they need a constant supply. When the oxygen saturation falls below 89 percent, or the arterial oxygen pressure falls below 60 mmHg—whether during rest, activity, sleep or at altitude—then supplemental oxygen is typically needed.

Detecting oxyHb, therefore, beneficially allows medical professionals to detect and diagnose oxygen-related medical conditions or health problems. The same is true with respect to the detection of deoxyhemoglobin and melanin. Any disorder causing hypoxemia may generate sufficient deoxyhemoglobin in the blood leaving the heart to produce central cyanosis. Typical etiologies are pulmonary edema, pneumonia, and intracardiac right-to-left shunts. The finding of central cyanosis increases greatly the probability of hypoxemia (likelihood ratio [LR]=7.4). Hypoxemia is defined as arterial deoxyhemoglobin level $\geq 2.38$ g/dL, corresponding to $SaO_2 \leq 80\%$ and $pO_2 \leq 45$ mm Hg in patients with normal amounts of hemoglobin. Meanwhile, issues with melanin levels are linked to several skin pigment disorders including albinism, melasma, vitiligo, Parkinson's disease, hearing loss, and pigment loss after skin damage.

The bed pan assembly 100 may include audio input and output structures 312, such as a microphone for receiving audio signals from a user and/or a speaker/transducer for producing alerts, e.g., audio, visual, or vibration upon detection of a fluid/liquid, of targeted properties, or when a threshold amount of a targeted property is reached or exceeded. In one embodiment, the analyzing sensors 204*a-n* include a microphone 316 operably configured to detect vibration within the at least one of the bottom wall 200 and the sidewall 104 of the bed pan housing 102 to measure flowrate of urine within the excretion storage cavity 108 as the targeted urine property. This feature beneficially assists in the accurate and prompt detection of targeted properties and/or threshold amount(s) of targeted properties. In another embodiment, the at least one analyzing sensor 204*e-f* is directly coupled to the sidewall 104, disposed proximal to, i.e., at or near, the upper surface 110, and operably configured to detect weight and movement of a user supported on the upper surface 110 of the bed pan housing 102. By being disposed proximally to the upper surface 110, the analyzing sensors 204e-f can detect the presence of urine or stools, and thresholds thereof, before any spillage or overflow occurs while simultaneously allowing for a reasonable quantity of urine or stool to accrue in the excretion storage cavity 108. Likewise, by being directly coupled to the sidewall 104, the analyzing sensors 204e-f are beneficially positioned to readily detect the presence of urine or stools, and thresholds thereof. The detection of weight and movement can be used by medical professionals to diagnose medical conditions, illnesses, etc. as well as to ensure the bed pan assembly 100 is being utilized properly and within the structural capabilities the bed pan assembly 100 is able to maintain.

In yet another embodiment, the at least one analyzing sensor 204e-f is directly coupled to the sidewall 104, disposed proximal to the upper surface 110, and operably configured to measure changes in electrical activity of a user's external anal sphincter, thereby predicting impending excretion of body waste from the user's body, the least one analyzing sensor 204e-f operably configured to communicate the electronic notification of the measured changes in electrical activity to the remote electronic communication device over the wireless network. Because electrical activity of the external anal sphincter changes during urinary or stool excretion, detecting fluctuations in such electrical activity can alert a user to an impending urinary or bowel movement and could help identify a medical issue, e.g., torn sphincter muscle, non-relaxing puborectalis, etc. The analyzing sensors 204e-f may comprise at least one surface electrode operably configured to measure the electrical activity or activation of the external anal sphincter.

The bottom wall 200 may further comprise a drain 218 defined thereon and with a filter cover 220 superimposing the drain 218; and a lower chamber 222 defined thereon and spatially separated from the excretion storage cavity 108 by the filter cover 220, wherein the at least one analyzing sensor 204b is disposed within the lower chamber 222 and operably configured to detect the targeted urine property. This feature beneficially allows the targeted urine property to be detected in scenarios where, by way of example and without limitation, a user excretes very small quantities of urine that are insufficient to reach the at least one analyzing sensor 204e-f in embodiments where the analyzing sensors 204e-f are directly coupled to the sidewall 104 and/or disposed proximal to the upper surface 110. The lower chamber 222 also functions to contain and enclose the urine in a chamber that is distinct from the excretion storage cavity 108 so as to allow for multiple consecutive uses of the bed pan assembly 100 without the need for emptying the contents of the excretion storage cavity 108 in between uses, and to substantially prevent spillage of the urine outside of the bed pan assembly 100.

Alternate embodiments of the present invention further include an assembly cover 1100 selectively removably couplable to the portable bed pan housing 102, the assembly cover 1100 having an upper assembly cover surface 1102, a lower assembly cover surface 1104 opposing the upper assembly cover surface 1102, and an aperture 1106 proportionately sized and shaped with respect to the excretion storage cavity 108. The aperture 1106 has dimensions proportionate to those of the excretion storage cavity 108 to provide a sufficiently large enough aperture through which a user may comfortably excrete a user's urine or stool. In accordance with a further feature, the bed pan assembly 100 also comprises a selectively removable retention member 1108 interposed between the assembly cover 1100 and the portable bed pan housing 102, the selectively removable retention member 1108 operably configured to retain a disposable waste bag thereon. The selectively removable retention member 1108 must have dimensions proportionate to those of the excretion storage cavity 108 to enable the selectively removable retention member 1108 to snugly fit and rest within the excretion storage cavity 108. The selectively removable retention member 1108 is operably configured to retain a disposable waste bag thereon or therein, which beneficially prevents a user from having to rinse, wash, sanitize, and/or clean the excretion storage cavity 108 after every use. Instead, the stool or urine waste/sample is excreted into a disposable waste bag that is retained on the selectively removable retention member 1108 such that the disposable waste bag may be removed from the selectively removable retention member 1108 after use, disposed of, and replaced with a new waste bag for subsequent use. Beneficially, the excretion storage cavity 108 remains substantially clean and sanitary for subsequent uses.

Therefore, the bed pan assembly 100 is operably configured to sample and analyze urine/stool for selected and/or desired targeted properties. Once detected, the circuit board assembly 300 is operably configured to initiate an alert or notification so that user(s), e.g., a nurse or physician, may take note of the quantity of targeted property and appropriately use the same in the medical diagnosis, prescription, and/or treatment of the patient. In this way, the bed pan assembly 100 beneficially facilitates and provides for "real time" medical monitoring of the patient and/or treatment resulting therefrom. FIGS. 5-13 depict several perspective and elevational views of one exemplary embodiment of the present invention.

What is claimed is:

1. A bed pan assembly with excretion analyzation comprising:
   a portable bed pan housing with:
   a bottom wall having a bottom inner surface;
   a sidewall having an inner sidewall surface surrounding the bottom inner surface to define an excretion storage cavity and having an upper surface surrounding the sidewall for supporting a weight of a user; and
   at least one analyzing sensor directly coupled to the sidewall of the bed pan housing, disposed proximal to the upper surface, and operably configured to detect at least one of a targeted stool property from a stool specimen received within the excretion storage cavity and a targeted urine property from a urine specimen received within the excretion storage cavity, operably configured to measure changes in electrical activity of a user's external anal sphincter, thereby predicting impending elimination of body waste from the user, communicatively couplable to a remote electronic communication device over a wireless network, operably configured to communicate an electronic notification of the measured changes in electrical activity to the remote electronic communication device over the wireless network, and operably configured to communicate an electronic notification of the at least one of the targeted stool property and the targeted urine property to the remote electronic communication device over the wireless network.

2. The bed pan assembly with excretion analyzation according to claim 1, wherein the at least one analyzing sensor is directly connected to the sidewall and further comprises:

a camera oriented at least partially toward the bottom inner surface, wherein the least one analyzing sensor is operably configured to detect excreta occult blood as the targeted stool property.

3. The bed pan assembly with excretion analyzation according to claim 1, wherein the at least one analyzing sensor is directly connected to the sidewall and further comprises:
a light spectroscopy unit operably configured to detect excreta occult blood as the targeted stool property.

4. The bed pan assembly with excretion analyzation according to claim 1, wherein the at least one analyzing sensor is directly connected to the sidewall and further comprises:
a light spectroscopy unit oriented at least partially toward the upper surface and operably configured to detect reflected light energy from a user's skin and relative or absolute concentration of at least one of oxyhemoglobin, deoxyhemoglobin, and melanin in the user's skin.

5. The bed pan assembly with excretion analyzation according to claim 1, wherein the at least one analyzing sensor further comprises:
a microphone operably configured to detect vibration within the at least one of the bottom wall and the sidewall of the bed pan housing to measure flowrate of urine within the excretion storage cavity as the targeted urine property.

6. The bed pan assembly with excretion analyzation according to claim 1, wherein:
the at least one analyzing sensor is directly coupled to the sidewall, disposed proximal to the upper surface, and operably configured to detect weight and movement of the user supported on the upper surface of the bed pan housing.

7. The bed pan assembly according to claim 1, wherein:
the upper surface of the sidewall is substantially planar and defines an upper plane parallel and non-coplanar with a bottom plane defined by a lower terminal surface of the bed pan housing, the lower terminal surface opposing the upper surface of the sidewall.

8. The bed pan assembly according to claim 1, wherein the bottom wall further comprises:
a drain defined by the bottom wall having a filter cover superimposing the drain; and
a lower chamber defined by the bottom wall and spatially separated from the excretion storage cavity by the filter cover, wherein the at least one analyzing sensor is disposed within the lower chamber and operably configured to detect the targeted urine property.

9. The bed pan assembly according to claim 1, further comprising:
an assembly cover selectively removably couplable to the portable bed pan housing, the assembly cover having an upper assembly cover surface, a lower assembly cover surface opposing the upper assembly cover surface, and an aperture proportionately sized and shaped with respect to the excretion storage cavity.

10. The bed pan assembly according to claim 9, further comprising:
a selectively removable retention member interposed between the assembly cover and the portable bed pan housing, the selectively removable retention member operably configured to retain a disposable waste bag thereon.

11. A bed pan assembly with excretion analyzation comprising:
a portable bed pan housing with: a bottom wall having a bottom inner surface, a drain defined by the bottom wall having a filter cover superimposing the drain, and a lower chamber defined thereon;
a sidewall having an inner sidewall surface surrounding the bottom inner surface to define an excretion storage cavity spatially separated from the lower chamber by the filter cover, and having an upper surface surrounding the sidewall for supporting a weight of a user; and
at least one analyzing sensor operably coupled to at least one of the bottom wall and the sidewall of the bed pan housing, operably configured to detect at least one of a targeted stool property from a stool specimen received within the excretion storage cavity and a targeted urine property from a urine specimen received within the excretion storage cavity, communicatively couplable to a remote electronic communication device over a wireless network, and operably configured to communicate an electronic notification of the at least one of the targeted stool property and the targeted urine property to the remote electronic communication device over the wireless network, the at least one analyzing sensor is disposed within the lower chamber and operably configured to detect the targeted urine property.

* * * * *